(12) United States Patent
Sawa et al.

(10) Patent No.: US 7,572,593 B2
(45) Date of Patent: Aug. 11, 2009

(54) TEST CELL FOR MAGNETIC IMMUNOREACTION ASSAY AND METHOD FOR PRODUCING SAME

(75) Inventors: Hiroshi Sawa, Nagoya (JP); Masanori Nagai, Nagoya (JP); Yoshinori Sugiura, Nagoya (JP); Shigenori Hamaoka, Fukuoka (JP); Kentaro Iwanaga, Anjo (JP); Keiji Enpuku, Fukuoka (JP); Kohji Yoshinaga, Kitakyushu (JP)

(73) Assignee: Inoac Corporation, Aichi-ken (JP)

( * ) Notice: Subject to any disclaimer, the term of this patent is extended or adjusted under 35 U.S.C. 154(b) by 351 days.

(21) Appl. No.: 11/087,648

(22) Filed: Mar. 24, 2005

(65) Prior Publication Data

US 2005/0214934 A1     Sep. 29, 2005

(30) Foreign Application Priority Data

Mar. 26, 2004    (JP)    ............................. 2004-093246

(51) Int. Cl.
    *G01N 33/53*    (2006.01)
(52) U.S. Cl. .................. 435/7.1; 435/7.4; 435/7.9; 435/174; 436/501; 424/94.1
(58) Field of Classification Search .............. 435/283.1; 436/173; 505/162, 191
    See application file for complete search history.

(56) References Cited

U.S. PATENT DOCUMENTS

| 5,324,481 | A | 6/1994 | Dunn et al. |
| 5,420,100 | A | * 5/1995 | Vittoria et al. ............... 505/162 |
| 7,033,841 | B1 | 4/2006 | Weitschies et al. |
| 2002/0132372 | A1 | 9/2002 | Enpuku |

FOREIGN PATENT DOCUMENTS

| JP | 2532670 | 6/1996 |
| JP | 9184841 | 7/1997 |
| JP | 9243641 | 9/1997 |
| JP | 11-508031 | 7/1999 |
| JP | 200304749 | 2/2000 |

OTHER PUBLICATIONS

Romaine et al. (Applied Phys. Lett, vol. 59, No. 20, Nov. 11, 1991, pp. 2603-2605).*
Lee et al. (Synthetic Metals, vol. 142, Apr. 13, 2004, pp. 243-249).*

(Continued)

*Primary Examiner*—Lisa V Cook
(74) *Attorney, Agent, or Firm*—Sughrue Mion, PLLC

(57) ABSTRACT

A test cell for magnetic immunoreaction assay, comprising a polymer having a quantity of residual magnetism of 15 pT or less, when a magnetic field is applied under a magnetic field of 0.1 T, and with a distance between a sample and a SQUID sensor being set at 1.5 mm, and a method for producing the test cell are provided. A test cell for magnetic immunoreaction assay, comprising a polymer having a metal content of 30 ppb or less, and a method for producing the test cell are also provided. A magnetic signal detected from a magnetic marker to be measured is not buried in or lost to the residual magnetic signal of the test cell itself, but data discrimination can be made clearly.

4 Claims, 8 Drawing Sheets

Relationship between weight of IgE and magnetic signal

OTHER PUBLICATIONS

Halzakis (Journal of Research Development, vol. 32, No. 4, Jul. 1988, pp. 441-453).*

Chatterjee et al (Journal of Magnetism and Magnetic Materials, vol. 246, 2002, pp. 382-391).*

Keiji Enpuku "Biological Immunoassay with a SQUID Magnetometer" Teion Kogaku (Cryogenics), vol. 38, No. 9, pp. 469-476 (2003).

Keiji Enpuku "Antigen-Antibody Reaction Assay with a SQUID system" Oyo Butsuri (Applied Physics), vol. 70, No. 1, p. 48 (2001).

* cited by examiner

Relationship between weight of IgE and magnetic signal

Relationship between amount of magnetic metal and quantity of residual magnetism Relationship of distance between magnetic sensor and sample to magnetic signal intensity Schematic view of apparatus Schematic view of sample Output waveform of SQUID sensor when the cell containing 3pg IgE sample was moved Output waveform of SQUID sensor when only the cell was moved Relationship between weight w of IgE and signal magnetic field $B_s$ detected by SQUID sensor

TEST CELL FOR MAGNETIC IMMUNOREACTION ASSAY AND METHOD FOR PRODUCING SAME

BACKGROUND OF THE INVENTION

This invention relates to a method for producing a test cell for use in a magnetic immunoreaction diagnostic apparatus using a magnetic marker. More specifically, the invention relates to the provision of a test cell for magnetic immunoreaction assay, which comprises a polymer having a quantity of residual magnetism, as measured by a SQUID sensor, of 15 pT or less, and also relates to a method for forming a test cell for magnetic immunoreaction assay from such a material.

In the field of so-called biomeasurement, such as detection of pathological microorganisms and cancer cells, DNA gene analysis, or detection of environmentally hazardous substances, it is common practice to measure the binding of a biological substance (antigen), which is to be measured using an immunoreaction, to a test reagent (antibody), which selectively binds to the biological substance, thereby measuring the type and amount of the antigen.

The detection of a biological substance has hitherto been performed by an optical technique which detects the biological substance with the use of an optical signal from an optically labeled antibody. In this optical technique, an optical marker such as a luminescent enzyme is addition-reacted with a test reagent (antibody), and light from the marker is measured to detect the biological substance. Currently, the lower limit of detection of a biological substance by this optical technique is said to be several picograms. Thus, the optical technique has become unable to fulfill a requirement for high sensitivity to those biological substances which are present in trace amounts of the order of several picograms or less at local sites or in the bloodstream. See, for example, the following patent documents or non-patent documents:

Japanese Patent No. 2532670
Japanese Patent Application Laid-Open No. 2000-304749
Japanese Patent Application Laid-Open No. 1997-184841
Japanese Patent Application Laid-Open No. 1997-243641
Japanese Officially Published Patent Gazette No. 1999-508031
K. Enpuku, "Bioimmunodiagnosis using SQUID", Journal of Cryogenics, Vol. 38, No. 9, pp. 469-476 (2003)
K. Enpuku. "Antigen-Antibody Reaction Measurement using SQUID", Journal of Applied Physics, Vol. 70, No. 1, p. 48 (2001)

As one of methods which satisfy the above requirement, a magnetic immunodiagnostic method using a high sensitivity magnetic sensor has been developed. Particularly, a superconducting quantum interference device, called SQUID, which makes use of a quantum effect (quantization of flux) appearing in a superconducting state, is attracting attention as a high sensitivity magnetic sensor, because it enables an extremely weak magnetic field to be measured.

An immunoreaction assay method by SQUID uses a magnetic marker constructed by addition-reacting an antibody with the surface of a polymer enclosing magnetic fine particles. This method measures by SQUID a feeble magnetic field signal issued from the magnetic marker when the antibody produces an antigen-antibody reaction with an antigen contained in a substance to be measured. Since the immunoreaction assay method by SQUID involves a high sensitivity sensor, this method is expected to provide sensitivity which is 100 times or more the sensitivity of a conventional fluorescent antibody assay method. Since the immunoreaction assay method by SQUID is a magnetic method, moreover, it can not only be expected to show high sensitivity, but it also is highly expected in that it can detect a biological substance even present in a solution. Furthermore, the conventional method of detection requires the step of washing off an unbound antibody after a labeled antibody is reacted with a biological substance. In the immunoreaction assay method by SQUID, by contrast, no signal comes from the unbound magnetic marker, and it suffices to detect a magnetic signal from only the marker bound to a biological substance. From the point of view of the washing-off step being omissible, the SQUID-based immunoreaction assay method is considered to be promising.

With the SQUID immunoreaction assay method, an antibody selectively binding to an antigen is used to bind the antigen and the antibody together. At this time, the antibody is addition-polymerized on the surface of a polymeric substance enclosing magnetic fine particles. The antibody with this feature is called a magnetic marker. The reaction between the antigen and the antibody is known from the detection of a magnetic signal from the magnetic marker. In the SQUID immunoreaction assay method, the magnitude of the magnetic signal is proportional to the amount of the magnetic marker bound to the antigen. To detect a weak antigen-antibody binding reaction with high sensitivity and at a high speed, therefore, it is necessary to measure a feeble magnetic signal as an index of detection of a trace reaction.

SUMMARY OF THE INVENTION

A first aspect of the present invention is a test cell for magnetic immunoreaction assay which comprises a polymer having a quantity of residual magnetism of 15 pT or less when a magnetic field is applied under the following conditions: a magnetic field of 0.1 T, and a distance of 1.5 mm between a sample and a SQUID sensor. More preferably, the test cell is a test cell for magnetic immunoreaction assay which comprises a polymer having a quantity of residual magnetism of 10 pT or less. Further preferably, the test cell is a test cell for magnetic immunoreaction assay which comprises a polymer having a quantity of residual magnetism of 5 pT or less.

A second aspect of the present invention is a test cell for magnetic immunoreaction assay which comprises a polymer having a metal content of 30 ppb or less.

Generally, in the magnetic immunodiagnostic method, an external magnetic field is applied to magnetize a magnetic marker. When a magnetic field of 0.1 T (tesla) is applied to a test cell, the test cell itself is inevitably magnetized. If many magnetic signals are detected from the test cell itself, therefore, it is impossible to distinguish between magnetic signals detected from the test cell and magnetic signals detected from the magnetic marker when an antigen-antibody binding reaction takes place. Thus, the immune reaction cannot be detected.

A relationship as shown in FIG. 1 exists between the weight of a substance to be measured (for example, human immunoglobulin E (IgE)) and a magnetic signal obtained from the magnetic marker bound to this substance. The magnetic signal is determined by applying a magnetic field of 0.1 T to the magnetic marker to generate residual magnetism from the marker, and measuring its magnetic signal by a SQUID sensor located at a position 1.5 mm from the sample. These conditions were employed for assay.

According to the relationship shown in the drawing, as the substance to be measured increases, the magnetic signal from the magnetic marker increases. At the same time, the amount of a magnetic signal tolerated as the quantity of residual magnetism of the test cell itself also increases.

According to the magnetic immunoreaction diagnostic method using the magnetic marker, even if the amount of the substance to be measured is 1 pg or less, its detection is possible. The relationship in FIG. 1 shows that when 0.3 pg of the substance to be measured is used, the magnetic signal obtained from the magnetic marker is about 20 pT ($20\times10^{-12}$ tesla). Hence, if the quantity of residual magnetism of the test cell itself, which appears as a noise, is 20 pT or more, the magnetic signal detected from the magnetic marker to be measured is buried in and lost to the residual magnetic signal of the test cell itself, thus resulting in a failure in distinction between the two types of magnetic signals. As a result, detection of an immunoreaction becomes impossible.

Accordingly, in the test cell used in the magnetic immunoreaction diagnostic apparatus using the magnetic marker, the quantity of residual magnetism of the test cell upon application of a magnetic field of 0.1 T to the test cell needs to be 15 pT or less.

In the conventional optical antibody testing method, an injection molded product of transparent polystyrene or a container made of transparent glass is used as a test cell. A polystyrene container commercially available from Nunc, for example, has a quantity of residual magnetism of 670 pT when measured by a SQUID sensor, and cannot be used for the magnetic immunoreaction assay method. When a test cell made of glass is measured by a SQUID sensor, its quantity of residual magnetism is 15 pT. Thus, this test cell falls within a range of usable test cells. However, after a sample is placed in the test cell and measured, the used test cell has to be incinerated, in principle, as a medical waste. The test cell made of glass, practically, cannot be incinerated, and thus cannot be used as a test cell in the magnetic immunoreaction diagnostic apparatus. Hence, a test cell made of plastic, which can be incinerated and is suitable for the magnetic immunoreaction assay method, is eagerly desired.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
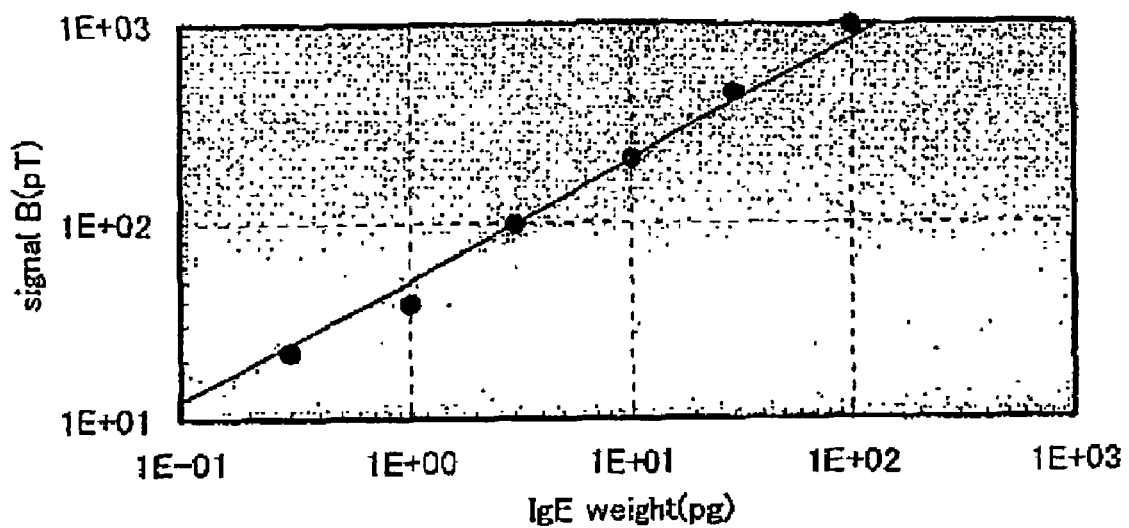
FIG. 1 is a view showing the relationship between the weight of IgE and a magnetic signal.

Generally, most of ordinary plastic materials use metal catalysts or metal compounds as compounding materials during the polymerization process, or their monomers make contact with reactors and piping, for example, made of stainless steel, with the result that metallic components are highly likely to enter the monomers as impurities. Various materials are conceivable as the materials for a test cell for magnetic measurement. If the processability of products and so on are actually considered, polyethylene, polycarbonate, polyamide, polystyrene, polyethylene terephthalate, polypropylene, and acrylic resin may be named as the materials.

However, these polymers contain a metal in an amount of the order of ppm. This metal content corresponds to a value in excess of 10-odd pT to 600 pT when calculated as a quantity of residual magnetism to be measured by a SQUID sensor.

Thus, plastic materials were selected, with attention being focused on a metallic component as a causative substance to be magnetized in a magnetic immunoreaction assay cell. Plastic materials, which are available and suitable as materials for a test cell for magnetic immunoreaction assay, were each evaluated based on judgment of history records, etc. of the steps where a metallic component was contained.

In the light of the results of the evaluation, acrylic resin, concretely, PMMA (polymethyl methacrylate), and high pressure polyethylene were selected as subjects for evaluation of materials for a test cell. High pressure polyethylene and polymethacrylate are both usable in the present invention. In consideration of physical properties, such as strength and rigidity after forming, PMMA is more preferred.

Monomer

A method for producing a monomer, for example, methyl methacrylate, is not limited, as long as it is a method which does not use a metal-containing catalyst. The monomer can be produced by a generally known method. For example, the acetone cyanhydrin method (ACH method) or the isobutylene method is preferred.

Polymer

A publicly known polymerization method can be selected, as appropriate, if it is a polymerization method which has no opportunity to contact a metal so that it fulfills the following condition: The quantity of residual magnetism, as measured by SQUID, of PMMA, which is a polymer obtained by polymerizing a purified monomer, for example, methyl methacrylate, should be 15 pT or less.

Concretely, with continuous bulk polymerization, a polymerization reaction is performed until a particular degree of conversion is reached and, with the unreacted monomer being deaerated and recovered by an extruder or the like, a polymer is obtained. According to this polymerization method, synthesis can be carried out without addition of a metal-based additive such as a polymerization aid. Since this polymerization method is a process performed in a closed system, it is minimal in contamination with impurities or other foreign objects, and gives a high purity polymer.

If the polymerization method by suspension polymerization is adopted, it Is possible to charge the monomer into pure water containing a dispersing agent, and perform polymerization while dispersing the monomer in a droplet form, thereby preparing beads. That is, a polymer can be prepared in the form of beads without contact with metal. If the entry of metal contained in pure water is managed, the entry of metal can be limited to a certain level or below.

Furthermore, solution polymerization, cast polymerization, or continuous cast polymerization can be used. Solution polymerization is a polymerization method by which a monomer is charged into a solvent, and heat-polymerized with the addition of a peroxide as a catalyst. Cast polymerization is a polymerization method by which synthesis of a polymer and formation of a sheet are performed at the same time. Cast polymerization is a method of manufacturing involving batch processing. Continuous cast polymerization is a polymerization method by which synthesis of a polymer and formation of a sheet are performed simultaneously. It is a method for producing a sheet continuously by forming a polymer on a belt conveyor.

The acrylic resin used in the present invention refers to an acrylic resin obtained by addition polymerization of a monomer consisting essentially of methacrylate ester, and includes copolymers of methyl methacrylate and other (meth)acrylic acid esters.

Figure 2:
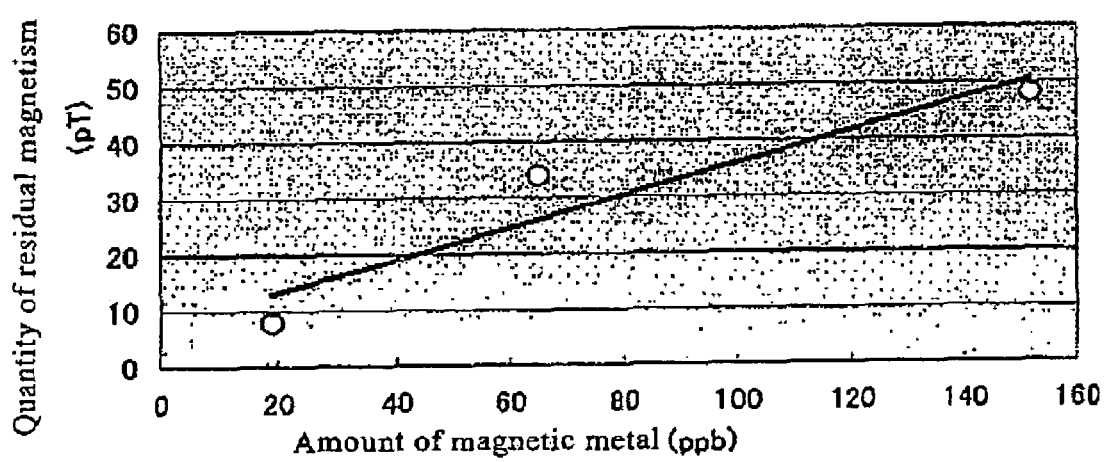
FIG. 2 is a view showing the relationship between the amount of a magnetic metal and a quantity of residual magnetism.

To know the relationship between the quantity of residual magnetism measured by the SQUID sensor and the magnetic metal content in the polymer, the amounts of a magnetic metal contained in the acrylic resin sheet having quantities of residual magnetism of 8 pT, 34 pT and 48 pT were measured by the ICP-MASS method. The results are shown in Table 3 and FIG. 2.

TABLE 3

Quantity of residual magnetism and metal content

| Quantity of residual magnetism (pT) | Metal content (ppb) | | | |
|---|---|---|---|---|
| | Fe | Co | Ni | Total |
| 48 | 100 | <1 | 52 | 152 |
| 34 | 53 | <1 | 12 | 65 |
| 8 | 18 | <1 | 1 | 19 |

The above results show that the correlation illustrated in the drawing is noted between the amount of magnetic metal contained in the acrylic resin and the quantity of residual magnetism. Based on the results, it is seen that the amount of magnetic metal should be limited to 30 ppb or less in order to fulfill the condition that the quantity of residual magnetism of the test cell for magnetic immunoreaction assay be 15 pT or less.

Method for Manufacturing the Test Cell: Forming of Sheet

In the present invention, a sheet-shaped plate material is produced, and then converted into a test cell by vacuum and/or pressure forming. For the production of the sheet-shaped plate material, various publicly known forming methods can be used. Concretely, glass plate casting, continuous casting, and extrusion are available. In casting (cast polymerization), a chain transfer agent and a polymerization initiator were blended with a monomer to prepare a monomer formulation. The monomer formulation was heated to make a viscous syrupy material. Then, the syrupy monomer formulation was cast into a mold held between two reinforced glass plates, and polymerized there. After polymerization, a plate-shaped polymer as a sheet was obtained. In continuous casting, a continuous cast plate is obtained by pouring a pre-polymerized syrup over a continuous belt made of stainless steel, and polymerizing it there. With extrusion, beads obtained by suspension polymerization, or pellets obtained by continuous bulk polymerization are brought into contact with steel products of an extruder, such as a screw, cylinder, screen and die, during an extrusion step, so that entry of metal into the resulting formed sheet was expected. However, pressure exerted on the formed product was an order of magnitude lower than the pressure by injection molding, and thus no entry of metal was detected. An acrylic polymer deposited on the screen of the extruder was examined, but did not show detection of metal.

Injection molding, because of its high injection pressure, involves much contamination with a metal component during contact between a molding machine and a polymer at the time of molding, and is thus unsuitable for uses of the present invention.

Protective Film

Generally, a protective film of paper or polymer is pasted to an acrylic resin sheet. Its object is to prevent scarring and staining. A protective film, which may be used for covering in the present invention, is greatly different from the above-mentioned protective film in that it is aimed at preventing deposition of impurities such as metals. The protective film is applied to one of or both of the face and back of the polymer sheet, and the thus protected sheet is subjected to vacuum and/or pressure forming for use as a test cell for magnetic immunoreaction assay. After forming, the protective film is not peeled from the test cell, but is maintained on the test cell until magnetic immunoreaction assay. Immediately before assay, the protective film is stripped off, and the test cell is used for assay.

The covering film (protective film) should not use a pressure sensitive adhesive in order to attain the object of the present invention, should be free from metallic components, and needs to adhere easily to both surfaces of the sheet, and easily peel off after forming. The protective film, which satisfies these conditions, can be used without any limitation. Adhesion of the protective film is preferably performed, for example, immediately after sheet production in the sheet manufacturing process for the polymer.

As stated in the aforementioned selection of materials, a high pressure polyethylene film containing no metallic components in the composition of the starting materials is preferred as the protective film.

As the polyethylene film, a pressure sensitive adhesion type film and a hot melt type film for general purpose use can be used. For the present film, low molecular weight polyethylene having a molecular weight of 1,000 to 2,000 or a wax having a molecular weight of 400 to 500 can be used. Further, ethylene-vinyl acetate may be contained as a pressure sensitive adhesion component.

With the pressure sensitive adhesion type film, when pressure is applied upon heating, the pressure sensitive adhesive migrates to the sheet, and dust tends to settle on the pressure sensitive adhesive that has migrated. Thus, the hot melt type film with ease of peeling and free from migration is more preferred.

Figure 4:
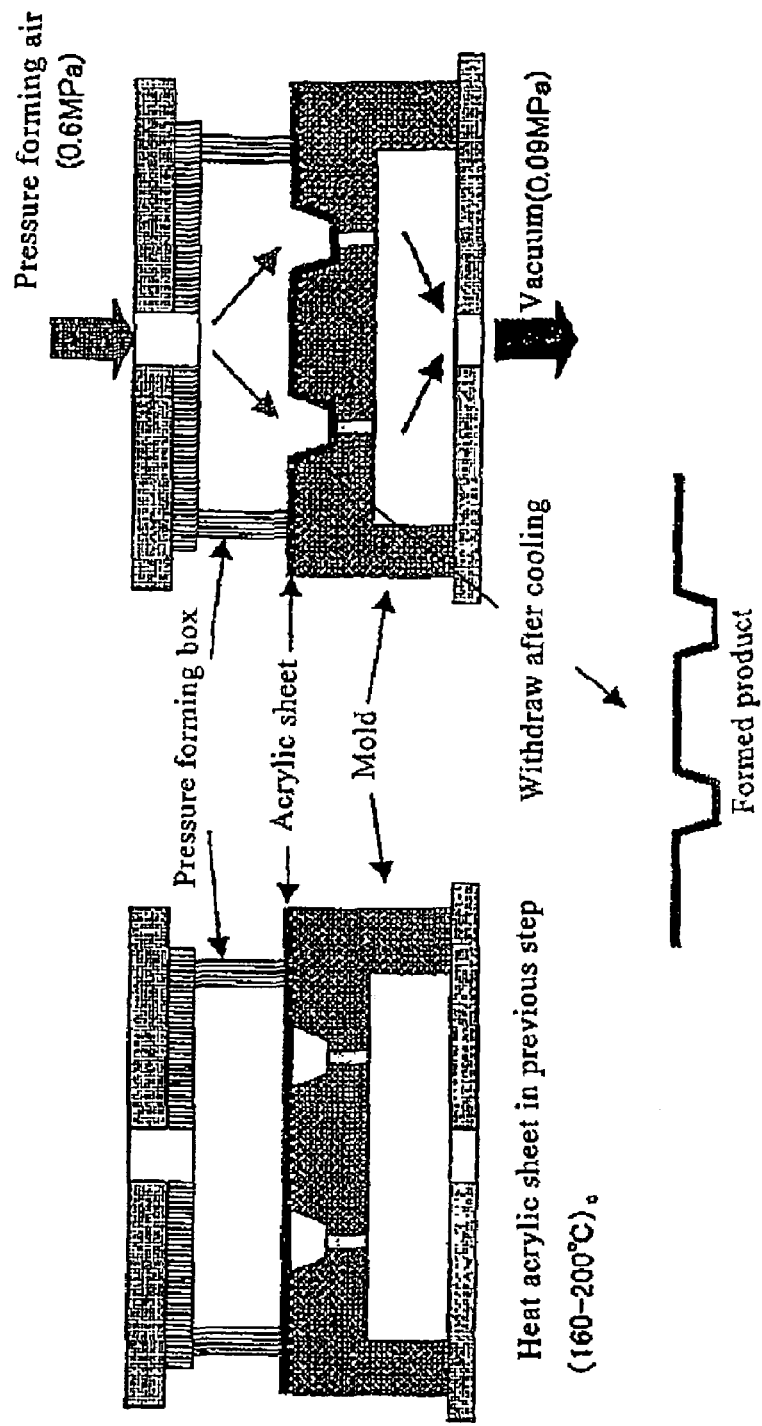
FIG. 4 is a view showing the outline of vacuum/pressure forming used in the present invention.

Method for Producing Test Cell: Forming of Test Cell/ Vacuum and/or Pressure Forming A test cell is produced from the sheet obtained by glass plate casting and extrusion. Various methods can be used for vacuum and/or pressure forming. Their examples include a female mold process in which the periphery of a heated and softened sheet is clamped by a pressure box, and the heated and softened sheet is pressed against a female mold in vacuo to impart the shape of the female mold to the sheet; a male mold process in which a heated and softened sheet is pressed against a male mold under vacuum to impart the shape of the male mold to the sheet; and a plug assist process in which shaping by a plug assist is carried out at the initial stage of forming, and then forming is completed with a female mold under vacuum. The present invention, moreover, adopted the female mold process, as well as a process in which vacuum drawing of a pressure box from below, and pressurization by air pressure from above were simultaneously performed, by means of a vacuum/pressure forming machine as illustrated in FIG. 4.

Furthermore, a laser cutter or a ceramic-coated cutting tool is used for cutting the test cell after forming. The use of this cutting method prevents contact of the test cell with metal.

The test cell for magnetic immunoreaction assay requires that surface treatment of the test cell can be performed so that an antibody binds to the test cell. Besides, the test cell needs to have quality characteristics and a shape suitable for use in a magnetic immunological testing apparatus.

Figure 3:
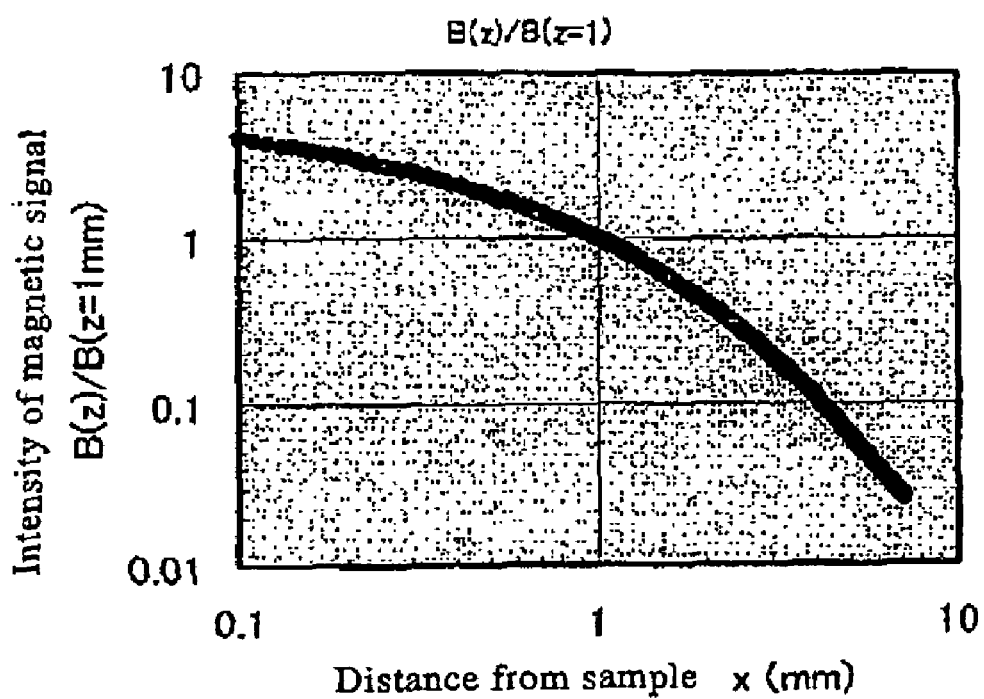
FIG. 3 is a view showing the relationship of the distance between a magnetic sensor and a sample to the intensity of the magnetic signal.

In connection with the shape of the test cell of the present invention, the most important item is the thickness of its bottom surface. The distance between a magnetic sensor and a sample varies according to the thickness of the bottom surface of the cell, and the magnitude of a magnetic signal changes according to the distance. This relationship is shown in FIG. 3. As shown in the drawing, the shorter the distance between the sample and the magnetic sensor, the greater the resulting magnetic signal becomes. That is, as small a thickness of the bottom surface of the cell as possible is preferred. However. If the thickness of the bottom surface of the cell is smaller than 0.1 mm, the rigidity of the cell cannot be ensured, and the cell is no more usable. If the distance between the magnetic sensor and the sample exceeds 1 mm, the magnitude of the resulting magnetic signal sharply decreases, impairing high sensitivity. Thus, the thickness of the bottom surface of the cell is 0.1 to 1.0 mm, preferably 0.1 to 0.5 mm.

EXAMPLES

The process from the selection of the resin to forming of the test cell will be described, and the results of application of the test cell to a SQUID apparatus will be mentioned.

Applicability as a test cell for magnetic immunoreaction assay was investigated closely. Acrylic resin and high pressure polyethylene can be used, but the high pressure polyethylene is not sufficient in terms of strength and binding to an antibody (Table 1). Hence, acrylic resin is preferred to high pressure polyethylene.

TABLE 1

Evaluation of residual magnetism, etc. of materials

| Name of resin | Quantity of residual magnetism (pT) | Intensity | Formability | Alcohol | Caustic soda | Incineration | Binding to antibody | Transparency | Overall evaluation |
|---|---|---|---|---|---|---|---|---|---|
| Comp. Ex. 1 Polyamide 6 Manufacturer: TORAY INDUSTRIES Product name: TORAY NYLON CM1021 | | | | | | | | | |
| 33 | X | ○ | ○ | ○ | ○ | ○ | ◎ | △ | X |
| Comp. Ex. 2 Polyamide 12 Manufacturer: Ube Industries Product name: UBE NYLON 123014B | | | | | | | | | |
| 120 | X | ○ | ○ | ○ | ○ | ○ | ◎ | △ | X |
| Ex. 1 Polyethylene (high pressure) Manufacturer: Japan Polyethylene Corporation Product name: NOVATEC LD LJ803 | | | | | | | | | |
| 12 | ○ | △ | ○ | ○ | ○ | ○ | △ | △ | △ |
| Comp. Ex. 3 Polycarbonate Manufacturer: Idemitsu Kosan Petrochemical Product name: TARFLON A1900 | | | | | | | | | |
| 125 | X | ○ | ○ | △ | ○ | ○ | ○ | ○ | X |
| Comp. Ex. 4 Polystyrene Manufacturer: PS Japan Product name: GPPS HF55 | | | | | | | | | |
| 670 | X | ○ | ○ | ○ | ○ | ○ | ○ | ○ | X |
| Ex. 2 PMMA (acrylate) Manufacturer: KURARAY Product name: COMOGLAS | | | | | | | | | |
| 8 | ○ | ○ | ○ | △ | ○ | ○ | ○ | ○ | ○ |
| Comp. Ex. 5 Glass | | | | | | | | | |
| 12~15 | ○ | ○ | △ | ○ | ○ | X | ○ | ○ | X |

Accepted ○
Rejected X
Insufficient △
Good ◎

To know the relationship between the quantity of residual magnetism and the metal content in the acrylic polymer, the amounts of metals (ferromagnets) contained in the acrylic resin sheet formed by the glass plate casting method were measured by the ICP-MASS method. The quantities of residual magnetism of the sample were 48 pT, 34 pT and 8 pT. The results are shown in Table 2.

TABLE 2

Quantity of residual magnetism and metal content

| Quantity of residual magnetism (pT) | Metal content (ppb) | | | |
|---|---|---|---|---|
| | Fe | Co | Ni | Total |
| 48 | 100 | <1 | 52 | 152 |
| 34 | 53 | <1 | 12 | 65 |
| 8 | 18 | <1 | 1 | 19 |

Next, the forming methods will be considered. First, injection molding was investigated. With injection molding, the test cell can be formed by one step without forming of an intermediate product, such as a sheet, from a polymer. However, the interior of the injection molding machine is in a high temperature (180 to 280° C.), high pressure (1,600 to 2,200 kg/cm$^2$) atmosphere, and the polymer makes contact with a screw, cylinder, mold, etc. made of steel, and rubs them, thereby inevitably causing entry of metals into the polymer. Actually, when a sheet was prepared by injection molding and its quantity of residual magnetism was measured by the SQUID sensor, a value of 50 to 100 pT was obtained, and deviated greatly from the desired range of the present invention.

Casting, in which a monomer is directly poured into a silicone mold and formed into a cell, was investigated. However, polymerization with heating required a considerable time, and thus was unsuitable for commercial mass production. At the same time, a method of forming which involves curing with UV rays was investigated, but the quantity of residual magnetism was great (65-110 pT).

Thus, a test cell was not to be directly obtained from the polymer. Instead, it was investigated to form a sheet as an intermediate product from the polymer, and then obtain a test cell by vacuum/pressure forming.

Production of Test Cell

An acrylic resin sheet (PARAGLAS, a product of KURARAY, dimensions 400 mm×400 mm, thickness 0.8 mm) formed by casting using a glass plate, and an acrylic resin sheet (COMOGLAS, a product of KURARAY, dimensions 400 mm×400 mm, thickness 1.0 mm) formed by extrusion were rendered ready for use. A polyethylene film was pasted onto both surfaces of each sheet.

A hot melt type film, as well as a general-purpose pressure sensitive adhesion type film, was used as the polyethylene film. Commercially available products 5370L (hot melt type, thickness 70 μm) of TORAY INDUSTRIES and #624KN and #622T (pressure sensitive adhesive films, thickness 70 μm) of Sekisui Chemical can be used as such films.

To produce the test cell, utmost care was taken net to avoid direct contact of metal with the sheet of the polymer. Concretely, a clamp coated with a nonmetallic material, such as ceramic, was used as a clamp for the polymer sheet, a ceramic heater was used as a heating board, a forming mold was made of aluminum and surface-coated with alumite, ceramic, TEFLON (registered trademark), or non-metallic coating, and air cleaned of moisture, metal, and oil by way of a plurality of stacked filters during vacuum/pressure forming.

The above-mentioned acrylic resin sheet by casting, and the acrylic resin sheet by extrusion were each predried for 12 hours at 60° C., and then mounted in a vacuum/pressure forming machine (a product of Asano Laboratories, product number: FKS-0631-20). Then, the mounted acrylic resin was heated up to 180° C., and then subjected to vacuum/pressure forming (degree of vacuum 0.09 MPa, pressure forming pressure 0.6 MPa, forming time 5 seconds). The temperature inside the mold of the vacuum/pressure forming machine was controlled so as to be maintained at 70° C. After completion of forming, cooling was performed, and the formed product was withdrawn from the forming machine.

The wall thickness of the bottom surface of a sample accommodating concave portion of the test cell was 0.4 mm. When the test cell was mounted in an immunoreaction assay apparatus using SQUID, and rotationally operated, the runout of the bottom surface of the cell was 0.1 mm or less.

In immunoreaction assay using SQUID, moreover, the sample bound to the magnetic marker was magnetized, and then the SQUID sensor was approached to the sample to measure the residual magnetism. On this occasion, the SQUID sensor was approached to the sample, from below the test cell, on the side of the bottom surface of the sample accommodating concave portion of the test cell opposite from the sample and without contact with the bottom surface. This positional relationship is the most preferred positional relationship for shortening the distance to the sample, because it is difficult in the design of the apparatus to insert the sensor from above into the sample accommodating concave portion of the test cell and approach the sensor to the sample.

In accordance with the distance between the SQUID sensor and the sample, the intensity of the magnetic signal varies. Thus, a shorter distance between the SQUID sensor and the sample is preferred, and when the thickness of the bottom surface of the sample accommodating concave portion of the test cell was set at 0.1 to 1.0 mm, the results of measurement were found to be satisfactory. As the distance between the SQUID sensor and the sample increases, the magnetic signal sharply decreases. The threshold for the sharp decrease is 1 mm. Thus, a large thickness of the bottom surface renders measurement impossible. If the thickness of the bottom surface of the sample accommodating concave portion of the test cell is smaller than 0.1 mm, the rigidity of the cell cannot be ensured.

Figure 5:
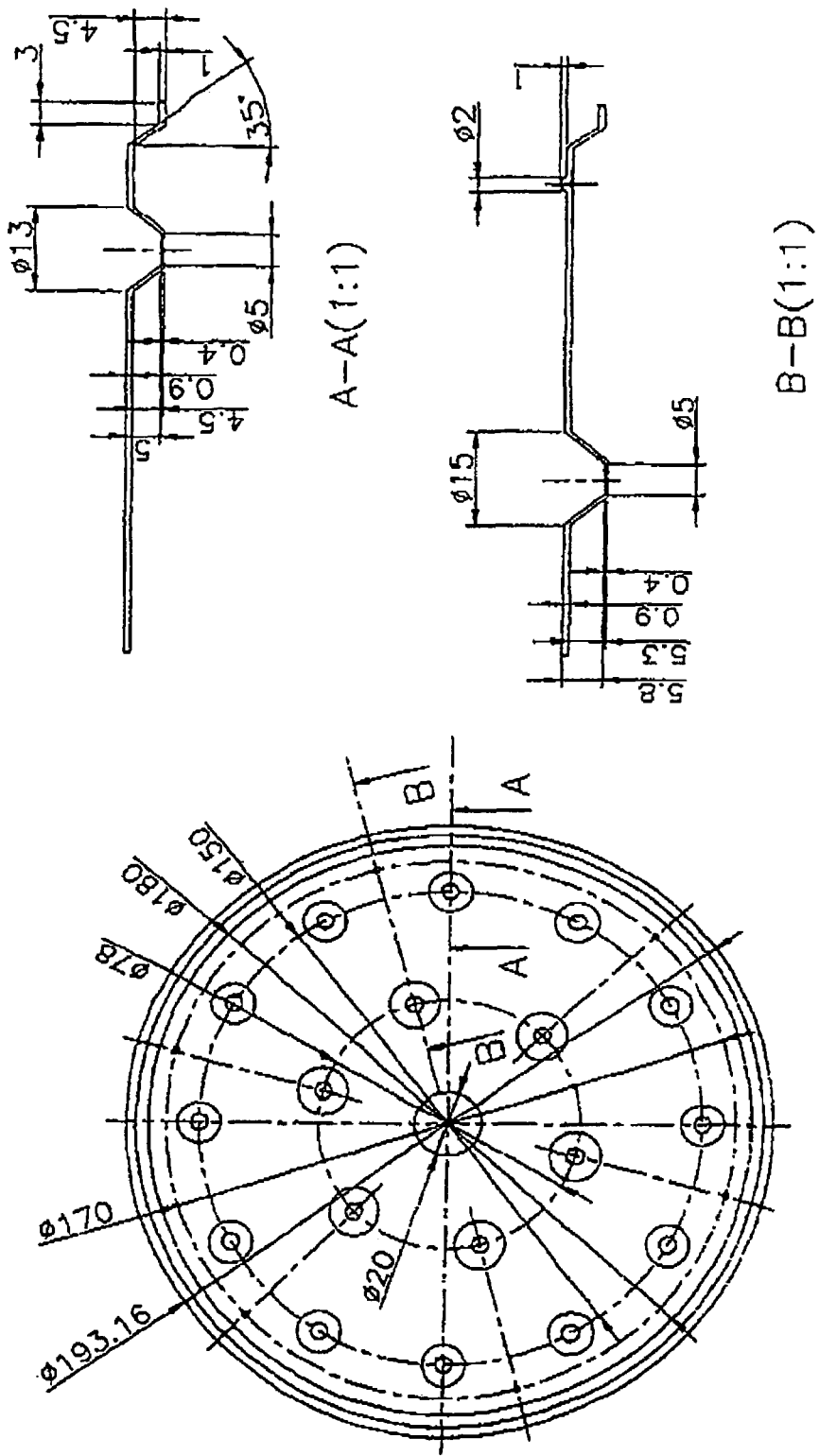
FIG. 5 is a view showing the concrete shape of a test cell as a formed product.

Finally. Table 4 shows the results of measurement, by the SQUID sensor, of the quantities of residual magnetism of the formed products (test cells) obtained by vacuum/pressure forming the protective film-covered sheets. A concrete shape of the test cell obtained as the formed product is shown, as an example, in FIG. 5.

TABLE 4

Quantities of residual magnetism of film-covered simultaneously formed products

| | Cast plate | | | Extruded plate | | |
|---|---|---|---|---|---|---|
| | KP | KFP | KFP-N | CP | CFP | CFP-N |
| Quantity of residual magnetism (pT) | 4-15 | 3-14 | 2-13 | 4-18 | 2-12 | 1-5 |
| Average quantity of residual magnetism (pT) | 9.8 | 7.9 | 5.4 | 7.4 | 5.9 | 2.9 |
| Reject rate (11 pt or more) | 60% | 30% | 7% | 20% | 10% | 0% |

The designations KP and CP in Table 4 mean the test cells free from the film. KFP and CFP denote the test cells integrally and simultaneously formed, with the pressure sensitive adhesive film pasted thereto. KFP-N and CFP-N denote the test cells integrally and simultaneously formed, with the hot melt type film pasted thereto.

The formed products obtained from the extruded sheets and the formed products obtained from the cast sheets were successful in markedly decreasing the reject rate. Concretely, the reject rate for the formed product obtained from the extruded sheet was 10%, while the reject rate for the formed product obtained from the cast sheet was 7%.

These results show that the formed product obtained from the extruded sheet and the formed product obtained from the cast sheet were both suitable as sheets for production of the test cell.

In the test cell of the present invention, it was found that magnetic immunoreaction assay data could be accurately collected by setting the thickness of the bottom of the sample accommodating concave portion at 0.1 to 1.0 mm. The test cell of the present invention was measured by the SQUID apparatus, and found to have a quantity of residual magnetism of 1 to 5 pT.

In the present invention, therefore, not only the quantity of residual magnetism of the material for the test cell was 15 pT or less, but the quantity of residual magnetism of the test cell after forming was also 15 pT or less. Accordingly, even if, in magnetic immunoassay apparatus, the substance to be measured is in a trace amount, and the magnetic signal detected from the magnetic marker to be measured is feeble, the assay value is not buried in or lost to the residual magnetic signal generated as a noise of the test cell itself.

Immunoreaction Assay by SQUID

Figure 6:
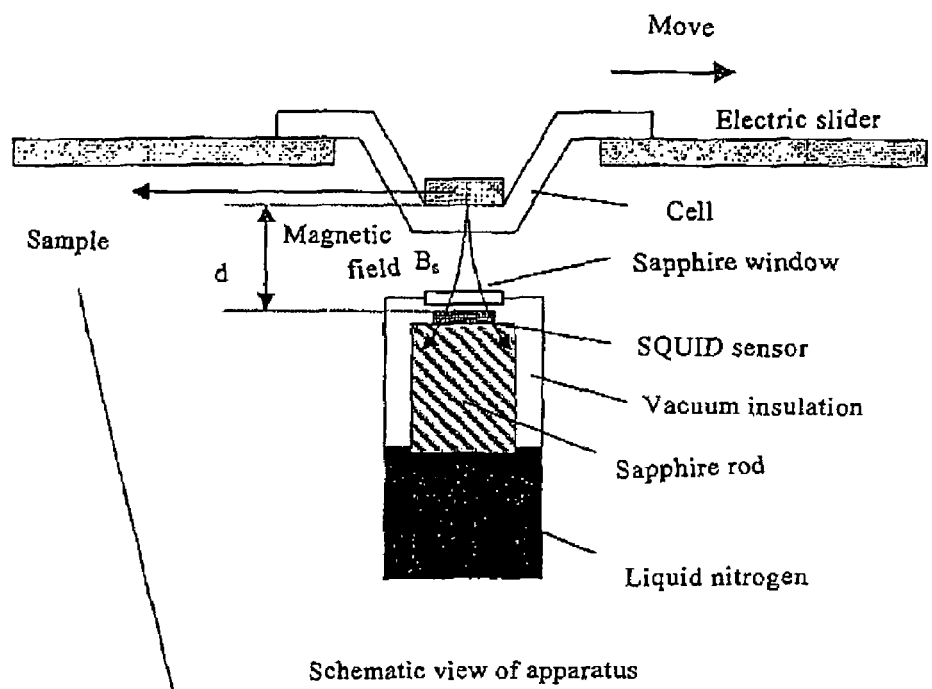
FIG. 6 is a view showing the outlined configuration of an immunoreaction assay apparatus by SQUID.

FIG. 6 shows the configuration of the apparatus. The SQUID sensor for detecting the magnetic field is prepared using a high critical temperature superconductor, and measures 3 mm×6 mm. The SQUID sensor needs to be cooled with liquid nitrogen. Thus, it is cooled by conduction cooling via a sapphire rod. Thermal shielding against the temperature in the environment surrounding the apparatus (i.e., room temperature) is by vacuum insulation, To bring the sensor and the sample into proximity, the upper surface of a nitrogen container is a thin sapphire window. This configuration enables the sample at room temperature to be measured.

The distance, d, between the sample and the SQUID sensor is given by the sum of the thickness of the bottom surface of the sample accommodating concave portion of the test cell, the distance between the cell and the sapphire window, the thickness of the sapphire window, and the distance between the sapphire window and the sensor. If the thickness of the bottom surface of the sample accommodating concave portion of the test cell is 0.4 mm, the distance d is d=1.5 mm. The following experiments were conducted under these conditions:

Preparation of Sample

Figure 7:
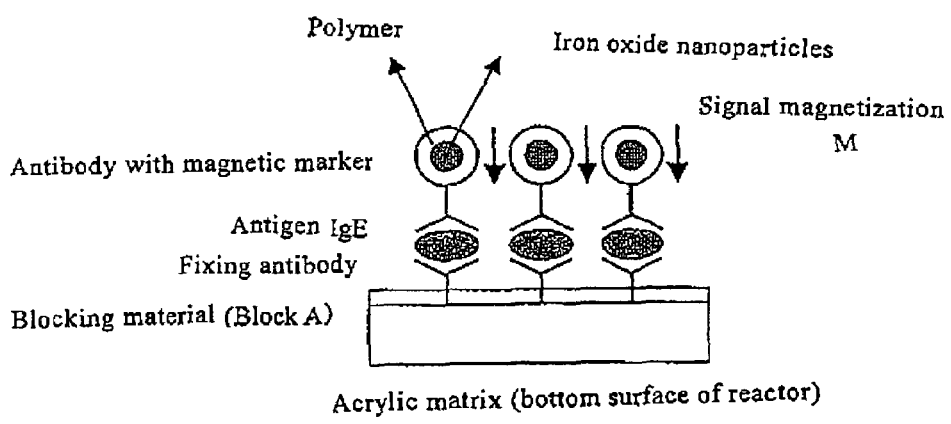
FIG. 7 is a schematic view of a sample.

FIG. 7 shows a schematic view of the sample used in the experiments. A sample for detection of IgE was prepared in accordance with the following procedure: First, the bottom surface of a reactor was coated with a blocking material (Block A). Then, a fixing antibody was caused to adhere. Then, 200 µl of a diluted solution containing IgE was placed in the reactor to bind the IgE and the fixing antibody together. After this binding, the solution was discarded, whereafter 200 µl of a solution containing a detection antibody with a magnetic marker was placed in the reactor. After the detection antibody and IgE were bound together, the solution was discarded, and the sample was thoroughly washed to remove the unbound magnetic marker. By this procedure, only the magnetic marker bound to IgE remains. Thus, a magnetic signal from the magnetic marker was measured, whereby the amount of IgE could be detected.

Measurement

When bound to IgE, the magnetic marker does not generate a magnetic signal. Thus, a magnetic field of the order of 1 kG was applied from the outside to generate residual magnetism in the magnetic marker. A signal magnetic field Bs was generated from a magnetization M due to the residual magnetism, and this magnetic field was measured by the SQUID sensor. To measure the signal magnetic field Bs, the reactor containing the sample was placed on an electric slider, and moved at a speed of 50 mm/s. During this period, the SQUID sensor was rendered stationary.

Figure 8:
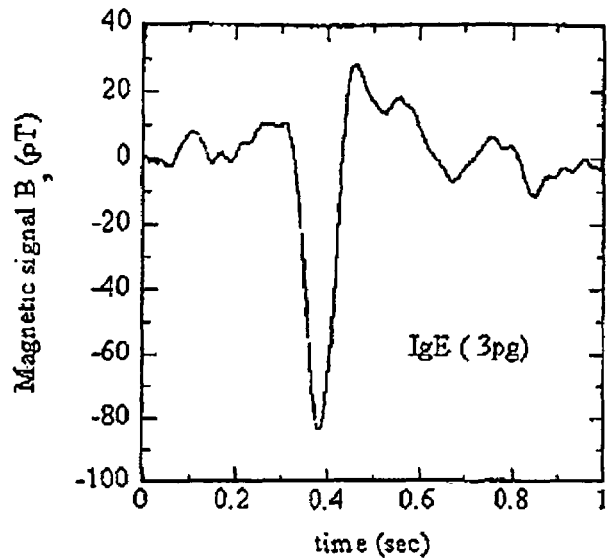
FIG. 8 is a view showing the output waveform of a SQUID sensor when a cell containing an IgE 3 pg sample is moved.

A signal waveform measured by the SQUID sensor in this case is shown in FIG. 8. IgE weighing 3 pg was used as a sample. As shown in the drawing, when the bottom surface of the sample accommodating concave portion of the test cell passes directly above the sensor, a great magnetic field signal is obtained. Since the peak value of the magnetic field is proportional to the amount of the magnetic marker, namely, the amount of the IgE poly-antibody in the sample, the amount of IgE can be detected from this peak value.

Figure 9:
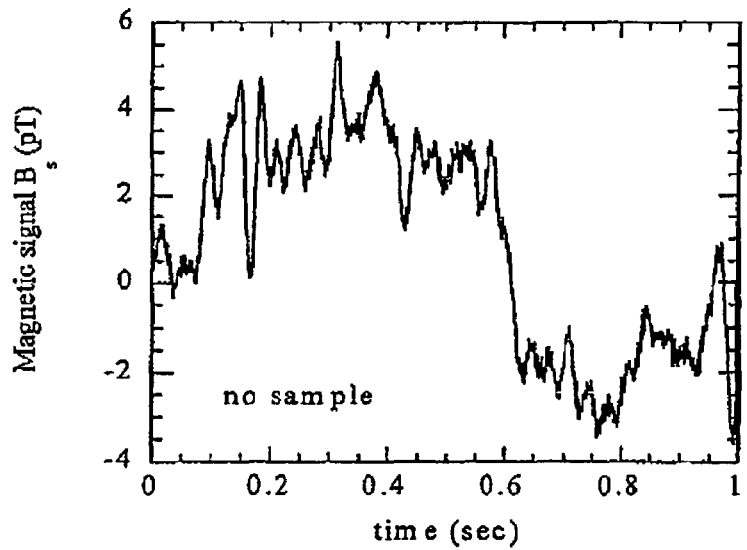
FIG. 9 is a view showing the output waveform of the SQUID sensor when only the cell is moved.

FIG. 9 shows the output waveform of the SQUID sensor in the absence of IgE. The output of the sensor in this case represents the sum of magnetic noises of the sensor and the reactor. As shown in FIG. 9, 10 pT or less is obtained as the magnitude of the magnetic noise. The magnetic noise of the SQUID sensor itself is of the order of 5 pT.

Figure 10:
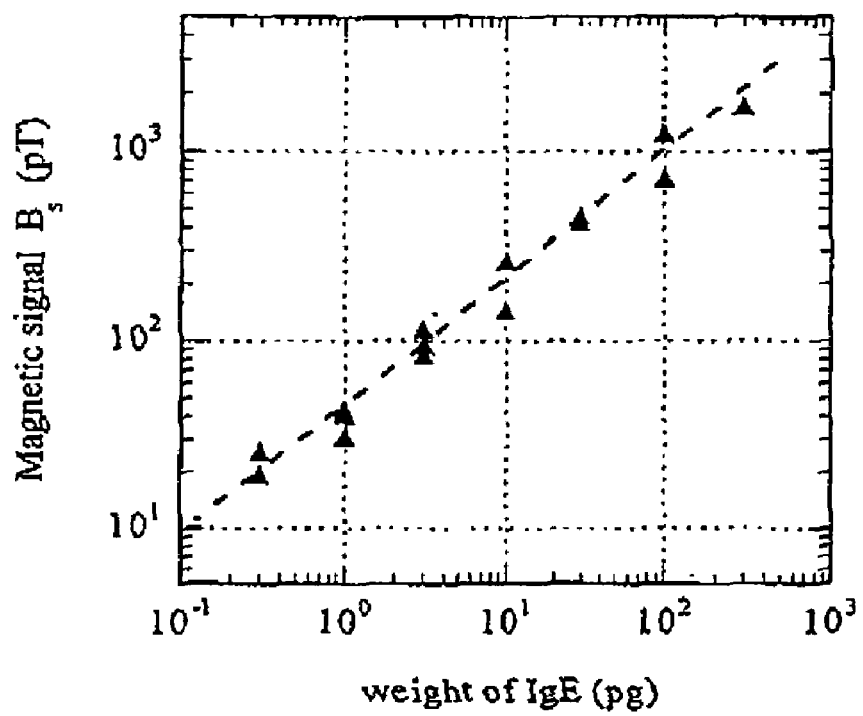
FIG. 10 is a view showing the relationship between the weight w of IgE and a signal magnetic field Bs detected by the SQUID sensor.

FIG. 10 shows the relationship between the weight w of IgE and the signal magnetic field Bs detected by the SQUID sensor, As the amount of IgE is changed in the range from 300 pg to 0.3 pg, a good correlation is obtained between the weight w and the signal magnetic field Bs. The magnitude of the signal magnetic field when the weight of IgE is 0.3 pg is Bs=20 pT.

In accordance with the present invention, a plastic material, which gives a quantity of residual magnetism of 15 pT or less to a test cell for magnetic immunoreaction assay, can be provided for the first time. According to a method for forming a test cell using this material, a magnetic signal detected from a magnetic marker to be measured is not buried in or lost to the residual magnetic signal of the test cell itself, but data discrimination can be performed clearly. Thus, a magnetic immunoreaction can be detected easily.

While the present invention has been described by the above embodiments, it is to be understood that the invention is not limited thereby, but may be varied or modified in many other ways. Such variations or modifications are not to be regarded as a departure from the spirit and scope of the invention, and all such variations and modifications as would be obvious to one skilled in the art are intended to be included within the scope of the appended claims.

What is claimed is:

1. A test cell,
consisting of a magnetically permeable resin material and a plastic film laminated on at least one face of the magnetically permeable resin material,
wherein the magnetically permeable resin material comprises a concave portion member and a bottom surface member formed in the concave portion,
wherein the magnetically permeable resin material and the plastic film have 30 ppb or less of magnetic metal content, wherein the magnetically permeable resin material and the plastic film have a quantity of total residual magnetism of 15 pT or less under a magnetic field of 0.1 T at a distance between the sample and a SQUID (superconducting quantum interference device) sensor of 1.5 mm, and wherein magnetic signals generated from an immunoreaction assay sample deposited on one surface of the test cell are detectable from the other surface of the test cell by using the SQUID sensor after removal of the plastic film, wherein the magnetically permeable resin material is poly(methyl methacrylate).

2. The test cell according to claim 1, wherein the thickness of the surface where the sample is deposited is 0.1 to 1.0 mm.

3. The test cell according to claim 1, wherein the test cell consists of a poly(methyl methacrylate) resin sheet cast over a glass plate and adhesive-free hot melt polyethylene films, which are removably laminated on both faces of the resin sheet, and which are vacuum and/or pressure formed into the test cell.

4. The test cell according to claim 1, wherein the plastic film comprises polyethylene having a molecular weight of 1000 to 2000 or a wax having a molecular weight of 400 to 500.

* * * * *